US012765755B2

(12) United States Patent
Jensen et al.

(10) Patent No.: US 12,765,755 B2
(45) Date of Patent: Oct. 20, 2026

(54) ENDOSCOPE WITH A BENDING SECTION HAVING A DISC FOR FIXING A STEERING WIRE

(71) Applicant: AMBU A/S, Ballerup (DK)

(72) Inventors: Thomas Bachgaard Jensen, Copenhagen (DK); Helga Künzl, Kissing (DE); Michael Kappler Hansen, Vallensbæk (DK); Martin Johst Christensen, Copenhagen Ø (DK)

(73) Assignee: AMBU A/S, Ballerup (DK)

( * ) Notice: Subject to any disclaimer, the term of this patent is extended or adjusted under 35 U.S.C. 154(b) by 387 days.

(21) Appl. No.: 18/037,958

(22) PCT Filed: Nov. 16, 2021

(86) PCT No.: PCT/EP2021/081818
§ 371 (c)(1),
(2) Date: May 19, 2023

(87) PCT Pub. No.: WO2022/106403
PCT Pub. Date: May 27, 2022

(65) Prior Publication Data

US 2023/0404375 A1 Dec. 21, 2023

(30) Foreign Application Priority Data

Nov. 23, 2020 (DE) ..................... 10 2020 130 953.8

(51) Int. Cl.
*A61B 1/005* (2006.01)
*A61B 1/008* (2006.01)

(52) U.S. Cl.
CPC .......... *A61B 1/0052* (2013.01); *A61B 1/0055* (2013.01); *A61B 1/0057* (2013.01); *A61B 1/008* (2013.01)

(58) Field of Classification Search
CPC ... A61B 1/0052; A61B 1/0055; A61B 1/0057; A61B 1/008
See application file for complete search history.

(56) References Cited

U.S. PATENT DOCUMENTS 3,190,286 A 6/1965 Stokes
3,625,200 A * 12/1971 Muller ................ A61B 1/0055 604/95.04

(Continued)

FOREIGN PATENT DOCUMENTS

| | | | |
|---|---|---|---|
| EP | 3498213 | A2 | 6/2019 |
| EP | 3628208 | A1 | 4/2020 |
| JP | 08-019618 | A | 1/1996 |

OTHER PUBLICATIONS

International Search Report and Written Opinion received for PCT Patent Application No. PCT/EP2021/081818, mailed on Feb. 22, 2022, 10 pages.

(Continued)

*Primary Examiner* — Michael J Carey
*Assistant Examiner* — Megan Elizabeth Monahan
(74) *Attorney, Agent, or Firm* — Faegre Drinker Biddle & Reath LLP

(57) ABSTRACT

An endoscope includes a distal tip unit, a handle, a shaft including a bending section made of a first material, and a steering wire for controlling a bending movement of the bending section. The bending section has segments, an inner lumen accommodating a working channel, and steering wire lumens adapted for accommodating the steering wire. The endoscope further includes a disc made of a second material which is different from the first material. The disc is arranged at a distal end of the bending section adjacent a lumen end of the steering wire lumens and has a plurality of openings including steering wire lumen openings configured for guiding the steering wire coming from the steering wire (Continued)

lumens therethrough, and locking openings configured for threading or twisting the steering wire therethrough. The steering wire is locked to the disc by the threading or twisting of the steering wire through the openings.

18 Claims, 2 Drawing Sheets

(56) References Cited

U.S. PATENT DOCUMENTS

| | | | | |
|---|---|---|---|---|
| 5,397,304 | A | 3/1995 | Truckai | |
| 6,482,149 | B1 * | 11/2002 | Torii | G02B 23/2476 600/141 |
| 8,162,934 | B2 * | 4/2012 | Potter | A61B 18/1492 604/95.04 |
| 9,155,451 | B2 * | 10/2015 | Smith | A61B 1/0055 |
| 9,585,641 | B2 | 3/2017 | Cooper et al. | |
| 9,737,687 | B2 * | 8/2017 | Armand | A61M 25/0138 |
| 10,321,804 | B2 | 6/2019 | Jacobsen et al. | |
| 10,524,868 | B2 | 1/2020 | Cooper et al. | |
| 2011/0125166 | A1 * | 5/2011 | Cooper | A61B 34/30 606/130 |
| 2014/0336685 | A1 | 11/2014 | Podmore et al. | |
| 2016/0367787 | A1 | 12/2016 | Van Hoven et al. | |
| 2018/0289242 | A1 * | 10/2018 | Dai | A61B 1/008 |
| 2019/0167070 | A1 * | 6/2019 | Ide | A61B 1/008 |
| 2019/0175875 | A1 * | 6/2019 | Mirzalou | A61M 25/0147 |
| 2019/0254504 | A1 * | 8/2019 | Ide | A61B 1/018 |
| 2019/0313882 | A1 * | 10/2019 | Nakayama | A61B 1/0055 |
| 2020/0100648 | A1 | 4/2020 | Jensen | |
| 2020/0316349 | A1 | 10/2020 | Smith | |

OTHER PUBLICATIONS

Search Report received for DE Patent Application No. 102020130953.8, mailed on Aug. 31, 2021, 14 pages (7 pages of English Translation and 7 pages of Original Document).

Examination Report issued in EP 21815159.5, dated Apr. 11, 2025, 6 pages.

* cited by examiner

ENDOSCOPE WITH A BENDING SECTION HAVING A DISC FOR FIXING A STEERING WIRE

CROSS REFERENCE TO RELATED APPLICATIONS

This application is a National Phase entry under 35 U.S.C. § 371 of International Application No. PCT/EP2021/081818, filed Nov. 16, 2021, which claims the benefit of and priority from German Patent Application No. DE 10 2020 130 953.8, filed Nov. 23, 2020; said applications are incorporated by reference herein in their entirety.

The present disclosure relates to an endoscope comprising: a distal tip unit configured to be inserted into a patient's body cavity; a proximal endoscope handle comprising an operating unit/handle wheel for steering the distal tip unit; an endoscope shaft/insertion tube connecting the endoscope handle and the distal tip unit and comprising a bending section; a working channel provided in the endoscope shaft and extending from the endoscope handle towards the distal tip unit; and a steering wire for controlling a bending movement of the bending section, the steering wire being connected to the operating unit and extending through the endoscope shaft. The bending section is made of a first material and comprises: a proximal end segment; a plurality of intermediate segments; a distal end segment; flexible hinge members provided between adjacent segments of the proximal end segment, the plurality of intermediate segments and the distal end segment; an inner lumen adopted for accommodating the working channel; and (dedicated) steering wire lumens adapted for accommodating the steering wire (in an assembled state of the endoscope), wherein the steering wire lumens have a lumen end (portion) at a distal end of the bending section, in particular in the distal end segment.

PRIOR ART

Endoscopes and similar specialized instruments such as bronchoscopes, arthroscopes, colonoscopes, laparoscopes, gastroscopes and duodenoscopes are well known from the state of the art and are used for visual examination and diagnosis of hollow organs and body cavities, as well as to assist in surgery, e.g. for a targeted tissue sampling. Basically, a distal tip unit of an endoscope, which is connected to an endoscope handle via an endoscope shaft, can be inserted into a hollow organ or body cavity to be investigated with the endoscope. Both reusable and disposable endoscopes are known from the state of the art.

Known endoscopes usually contain (a) steering/control wire(s) that is/are pulled and released to bend a (flexible) bending section of the endoscope, such as a flexible shaft, in order to tilt the distal tip unit. The rotating force being applied to (a) handle wheel(s) provided at the endoscope handle by a user is basically transmitted into a pulling force acting on the steering wire in an axial direction of the steering wire. Thereby, the connection of the steering wire to the handle wheel is essential for transmitting the rotating force from the handle wheel to the steering wire.

In addition, for guiding medical instruments, such as forceps, into the patient's body cavity, a working channel is arranged or formed within the endoscope shaft. In known endoscopes, this working channel is usually implemented/formed as a flexible tube arranged/accommodated/supported in a lumen extending through the endoscope shaft in a longitudinal direction from the endoscope handle to the distal tip unit. Such a conventional endoscope is disclosed for example in U.S. Pat. No. 10,321,804 B2. In particular, U.S. Pat. No. 10,321,804 B2 discloses a bending section of an endoscope molded in a single piece of polymer material. The bending section comprises a number of bending segments kept/held together by bendable hinges. Steering wires are threaded through holes in the wall of the bending segments. The holes are usually already formed in the molding process. Further, the bending section comprises one lumen for a working channel and one lumen for electrical wires.

It is basically known that a middle portion of a steering wire may form a loop at a distal end of the bending section and two ends/end portions of the steering wire extend towards the handle and can be actuated by a user (e.g. via the handle wheel). In such a design there is basically the danger that the steering wire cuts into the bending section, in particular when the steering wire is fixed/locked at a bending section which is made from a polymer/which is a molded polymer material part. This is however the typical/usual case for single-use endoscopes. There is thus the problem in prior art single-use endoscopes that the steering wire may cut in the bending section of the endoscope. Moreover, an assembly process, in particular a threading of the steering wires may be complicated in such prior art single-use endoscopes.

Another document, EP 3 498 213 A2, discloses a minimally invasive surgical instrument, in particular endoscope or laparoscope, comprising a wrist having a flexible tube bent by actuation cables. The flexible tube permits bending in pitch and yaw by pulling the actuation cables. Six cables are provided making U-turns at a distal end of the flexible tube. The wrist may include a rigid distal termination disk or other reinforcement that is substantially more rigid than the flexible tube to evenly distribute cable forces to the flexible tube. In the endoscope disclosed in EP 3 498 213 A2 it has turned out that when two lumens through which a steering wire runs are arranged closely together and the steering wire makes two 90° kinks in a short distance on a rigid disk there is the danger that the steering wire breaks/tears/fails. Moreover, forming a loop consisting of only two 90° kinks has the disadvantage that the steering wire is not appropriately fixed/locked at the distal end of the bending section.

BRIEF DESCRIPTION OF THE DISCLOSURE

The tasks and objectives of the present disclosure are to eliminate or at least to reduce the disadvantages of the prior art. In particular, an endoscope shall be provided, in which a steering wire is appropriately secured/locked at a distal end of a bending section of the endoscope. Both, cutting of the steering wire into a material of the bending section and breaking/tearing of the steering wire shall be suitably prevented. In addition, an assembly process of the endoscope shall be simplified/eased.

The tasks and objectives are solved by an endoscope in accordance with claim 1. Advantageous embodiments are claimed in the dependent claims and/or are explained below.

In the present disclosure, "distal" basically means "in a direction away from a user/physician towards a patient" and "proximal" basically means "in a direction towards the user/physician away from the patient".

The present disclosure relates to an endoscope, in particular single-use endoscope, comprising: a distal tip unit configured to be inserted into a patient's body cavity; a proximal endoscope handle comprising an operating unit (handle wheel) for steering the distal tip unit; an endoscope shaft (insertion tube) connecting the endoscope handle and the distal tip unit and comprising a bending section; a working channel provided in the endoscope shaft and extending from the endoscope handle towards the distal tip unit; and a steering wire, preferably formed as a steel wire, for controlling a bending movement of the bending section. The steering wire is connected to the operating unit and extends through the endoscope shaft. The bending section is made of a first material and comprises: a proximal end segment; a plurality of intermediate segments; a distal end segment, preferably connected to the distal tip unit (directly or via another component/part); flexible hinge members provided between adjacent segments of the proximal end segment, the plurality of intermediate segments and the distal end segment; an inner lumen adopted for accommodating the working channel; and (dedicated) steering wire lumens adapted for accommodating the steering wire (in an assembled state of the endoscope). The steering wire lumens have a lumen end (end of the steering wire lumen, where the steering wire exits the steering wire lumen) at a distal end of the bending section, in particular in the distal end segment. The endoscope further comprises a (separate) disc/locking disc made of a second material, which is different from the first material. The disc is arranged at the distal end of the bending section, preferably in the distal end segment, adjacent the lumen end of the steering wire lumens and has a plurality of openings/holes. The openings comprise: steering wire lumen openings/holes configured for guiding the steering wire coming from the steering wire lumens there through; and locking openings/holes configured for threading or twisting the steering wire there through. The steering wire is fixed/fixated/locked to the disc by the threading or twisting of the steering wire through the openings (i.e. through the steering wire lumen openings and the locking openings).

In other words, the present disclosure provides an endoscope, in which a steering wire forms a loop at the distal end of the bending section. In order to prevent that the steering wire cuts into the bending section a separate plate/disc is provided/arranged at the distal end of the bending section. The application of the disc in particular prevents that the steering wire will cut into the bending section material when high forces are conveyed through the steering wire. The separate disc is made from a different, especially harder/more rigid, material compared to the bending section. The material of the disc is preferably chosen so as to not allow/to prevent a cutting of the steering wire into the disc. In order to prevent that the steering wire tears/breaks, the steering wire runs through/is threaded/twisted through locking openings provided in the disc in the assembled state of the endoscope. Preferably, the steering wire is threaded through at least two locking openings provided in the disc, so that the steering wire basically forms a W-shaped (double-U-shaped) loop (no U-shaped loop) in the assembled state of the endoscope. The steering wire may be threaded through the disc before the disc is arranged in the distal end of the bending section, so that an assembly process is eased/simplified to a great extent.

According to the present disclosure, the disc is arranged at the distal end of the bending section. In particular, it is especially preferred to arrange the disc in the distal end segment. However, the disclosure is not limited to the disc being arranged in the distal end segment. E.g. the disc may be arranged at a distal end surface of the bending section/of the distal end segment, and thus not in/inside the distal end segment. Moreover, it is conceivable to arrange a component/part distally with respect to the distal end segment, so that said component/part is arranged between the distal end segment and the disc, and the disc may be arranged at/in said component/part. Said component/part may e.g. have a hardness which is equal to that of the (remainder of the) bending section.

The inner lumen of the bending section is preferably a central passage through the segments (the proximal end segment, the plurality of intermediate segments and the distal end segment) of the bending section and is adapted/has a cross-sectional shape to accommodate the working channel/a bendable tube providing the working channel.

The inner lumen/central passage preferably has a non-circular cross sectional shape. In other words, a radial extension of the inner lumen is preferably smaller in a circumferential area of the bending section where the steering wire lumen(s) is/are provided compared to a circumferential area of the bending section where the steering wire lumen(s) is/are not provided, seen in a cross-sectional view. Once again differently said, the inner lumen preferably extends into a bending section material (in a circumferential area) between two steering wire lumens.

Particularly preferred, the inner lumen forms a four-leaf clover, seen in a cross sectional view.

The bending section is preferably made from a polymer material. This means that the first material is preferably a polymer/plastic material. Especially preferred the bending section is made from a thermoplastic polymer, e.g. polystyrene (PS), polycarbonate (PC), acrylonitrile butadiene styrene (ABS), polyoxymethylene (POM), etc. However also other (thermoplastic) polymers are basically conceivable.

In particular, the bending section is formed/molded as a one-piece/single piece/integral part of a polymer material. This means, that it is preferable when the proximal end segment, the plurality of intermediate segments, the distal end segment and the hinge members are formed in one piece/one part/integrally. The bending section is especially preferred an injection molded part/is manufactured using an injection-molding process.

According to the present disclosure, in order to prevent that the steering wire cuts into the bending section (made of the first (polymer) material), a separate (locking) disc/plate made of the second material is provided/arranged at the distal end of the bending section.

The disc is preferably a separate part (is separate from the bending section) and is configured to be removably accommodated/inserted in/into the distal end, in particular the distal end segment, of the bending section. Said differently, the disc is preferably placed/can be placed at a distal end of the bending section where the (dedicated) steering wire lumens of the bending section end.

It is particularly advantageous when the disc abuts on a distal surface provided in the distal end, in particular the distal end segment, of the bending section.

The second material (from which the disc is made) is preferably harder/more rigid/has a higher modulus of elasticity/elastic modulus than the first material (from which the bending section is made).

According to an especially preferred embodiment the disc is made from a metal. The disc is preferably (pressure) hardened, e.g. cold-rolled. The disc may for example be cut from a (cold-rolled) steel plate. The disc may be manufactured by laser cutting. Alternatively the disc may be manufactured by punching. It is also conceivable that the disc is manufactured using an etching process/technology (similar to a process applied in manufacturing printed circuit boards). When using an etching process/technology, it is necessary to appropriately design the etching process in order to avoid removal of hardened layers of the disc. To sum up, the disc is preferably punched/laser-cut/etched from a (cold-rolled/pressure hardened) steel plate.

The present disclosure is however not limited to the disc being made from a metal. In particular, other materials are conceivable, as long as the material of the disc (the second material) is more rigid/harder than the material of the bending section (the first material). For example, the disc may be made from a polymer harder/more rigid than the polymer of the bending section. Alternatively, the disc may also be made from a composite material, in particular a fiber composite material.

When applying a polymer/composite material the hardness can be appropriately defined according to the ASTM D2240 standard for shore durometer hardness testing, applying a type D scale for example. When applying said standard the small dimensions of the disc and the bending section have to be appropriately considered. In particular, modifications like applying smaller dimensions of the material under test and/or applying a lower load on the indenting foot might be necessary (as long as for both materials the same material dimensions and the same load is applied).

It is also conceivable that the disc is made from a ceramic.

The disc preferably has a thickness of less than 1 mm, preferably of less than 0.5 mm, especially preferred of about 0.3 mm.

The disc is preferably configured and provided for locking/fixing/fixating the steering wire(s).

Especially preferred, a middle section/portion of the steering wire is fixed/locked to the disc. In this case, a first end section/portion of the steering wire may extend from the disc through a first steering wire lumen of the plurality of steering wire lumens, and a second end section of the steering wire may extend from the disc through a second steering wire lumen of the plurality of steering wire lumens, the first end section and the second end section extending towards the endoscope handle where they are fixed at/to the operating unit.

The disc preferably has a round, essentially annular shape with a large center opening/hole. It is preferred when the center opening has a non-circular shape. Especially preferred, the center opening has a four-leaf clover shape (corresponding to the shape of the inner lumen of the bending section).

The disc may comprise—in addition to the center opening—the steering wire lumen openings and the locking openings. The steering wire lumen openings and the locking openings are preferably distributed appropriately over a circumference of the disc.

A size/diameter of the steering wire lumen openings may be greater/bigger than a size/diameter of the locking openings.

The steering wire lumen openings may be placed/arranged/provided to correspond with the (dedicated) steering wire lumens. Said differently, the steering wire lumen openings of the disc are preferably placed directly over/above/adjacent the steering wire lumen end in the bending section in the assembled state of the endoscope. For example, an axis of a (round/circular) steering wire lumen opening of the disc may coincide with an axis of the steering wire lumen.

Preferably, the bending section is configured for two-plane bending/is configured to bend in at least four directions, in particular in an up-direction, in a down-direction, in a right-direction and in a left-direction. However, also one-plane bending is conceivable.

According to a preferred embodiment, the bending section may comprise four steering wire lumens and two steering wires may be provided. In other words, the bending section may be controlled by two steering wires arranged in four steering wire lumens. Each steering wire of the two steering wires may be accommodated in two steering wire lumens in the assembled state of the endoscope, and a middle section of each steering wire may be fixed to the locking disc.

According to the preferred embodiment a first end section of a first steering wire of the two steering wires extends from the disc through a first steering wire lumen of the four steering wire lumens, a second end section of the first steering wire extends from the disc through a second steering wire lumen of the four steering wire lumens, a first end section of a second steering wire extends from the disc through a third steering wire lumen of the four steering wire lumens, and a second end section of the second steering wire extends from the disc through a fourth steering wire lumen of the four steering wire lumens.

The disc may comprise a plurality of, in particular four, steering wire lumen openings/holes and a plurality of, in particular four, locking openings/holes.

The steering wire lumen openings/holes may be essentially equally spaced along/around a circumference of the disc (e.g. approximately 90° in case four steering wire lumen openings are provided).

Preferably, in a first angular area between two steering wire lumen openings two locking openings are provided. In addition, in a second angular area between two (other) steering wire lumen openings two locking openings may be provided. The first angular area may be arranged diametrically opposed with respect to the second angular area.

It is advantageous if—in the assembled state of the endoscope—the steering wire coming from a first steering wire lumen of the bending section and from a first steering wire lumen opening of the disc (is guided/pulled/) runs over/along a distal surface of the disc, is threaded into a first locking opening of the disc, runs over/along a proximal surface of the disc, is threaded into a second locking opening of the disc, runs over the distal surface of the disc again, and then runs/is threaded into a second steering wire lumen opening of the disc and into a second steering wire lumen of the bending section.

Basically, according to a first embodiment the steering wire lumen of the bending section may have an essentially round/circular (cross-sectional) shape, the steering wire lumen openings of the disc may have an essentially round/circular shape and the locking openings may have an essentially round/circular shape. In particular the steering wire lumen(s) may have essentially the same size and shape as the steering wire lumen openings of the disc.

However, according to a second embodiment, the steering wire lumen openings/holes of the disc may also have an oval/elongated hole/slotted hole shape. In particular, the steering wire lumen openings may be elongated/slotted holes and may comprise semicircles at its ends having essentially the same radius as the steering wire lumen (having the round/circular cross sectional shape).

In particular, in the assembled state of the endoscope the steering wire may be bent twice/may have two kinks (a first kink and a second kink) when exiting the steering wire lumen, wherein the first kink is formed when the steering wire is guided/pulled/runs via an edge provided between the steering wire lumen and the distal surface provided in/at the distal end, preferably in the distal end segment, of the bending section, and the second kink is formed when the steering wire is then guided/pulled/runs via an edge formed by the steering wire lumen opening of the disc having the elongated/slotted hole shape.

At the first kink the steering wire may be angled by a first angle of less than 90° and at the second kink the steering wire may be angled by a second angle of less than 90°. Especially preferred a sum of the first angle and the second angle may be 90°.

Therefore, a radius of the 90° bend where the steering wire enters/leaves the steering wire lumen may be larger in case the steering wire lumen holes have the elongated/slotted hole shape compared to a case in which the steering wire lumen holes have the round/circular shape.

According to the second embodiment, the steering wire may be supported both by the disc and by the distal surface provided in/at the distal end (the distal surface of the distal end segment) of the bending section (the underlying polymer material of the bending section).

The second embodiment has the particular advantage that the steering wire has a still higher tensile strength compared to the first embodiment. In particular, according to a test performed by the inventors, the tensile strength was defined as the load where the first of nineteen individual threads in a steering wire breaks. Applying the oval/slotted hole shaped steering wire lumen holes of the second embodiment a tensile strength of 140 N resulted/was measured. Applying the round steering wire lumen holes of the first embodiment a tensile strength of only 90 N resulted/was measured. Therefore, applying the second embodiment a breaking/tearing of a steering wire is even more prevented.

Basically, in an outer circumference of the disc at least one recess, preferably two recesses, may be provided, the recess being configured/provided for assisting in aligning the disc with respect to the distal end/the distal end segment of the bending section.

In addition, the distal end/the distal end segment of the bending section may comprise an alignment rib, preferably two alignment ribs, being configured and provided for assisting in aligning the disc with respect to the distal end/the distal end segment of the bending section. The alignment rib may be formed as a protrusion provided on an inner shell surface of the distal end/the distal end segment. The protrusion may extend in an axial direction of the distal end/the distal end segment.

The alignment rib may accommodate the recess provided in the disc in the assembled state of the endoscope. Therefore, a shape of the recess of the disc may be adopted/may correspond to a shape of the alignment rib, so that the disc is accommodated in the distal end/the distal end segment in a twist-proof way (cannot be rotated) in the assembled state of the endoscope.

Moreover, the distal end/the distal end segment of the bending section may comprise a press fit rib, preferably a plurality of press fit ribs, especially preferred four press fit ribs, the press fit rib being configured and provided for establishing a press fit connection between the disc and the distal end/the distal end segment. The press fit rib may be formed as a protrusion provided on the inner shell surface of the distal end/the distal end segment of the bending section. The press fit rib may extend in an axial direction of the distal end/the distal end segment. Further, the press fit rib may be configured to establish a press fit connection with an outer circumference of the disc in the assembled state of the endoscope.

An extension of the press fit rib towards the inside of the distal end/the distal end segment is preferably smaller than an extension of the alignment rib towards the inside of the distal end/distal end segment.

Preferably, the distal end/the distal end segment further comprises a wire cutout, the wire cutout being a recessed portion with respect to the distal surface of the distal end segment/the distal surface provided in the distal end and being provided under/adjacent the locking holes of the disc (in an axial direction of the distal end/the distal end segment) in the assembled state of the endoscope.

The (single-use) endoscope of the present disclosure is preferably a larger scope/endoscope like a gastroscope or a colonoscope. For such endoscopes it is especially important to eliminate the risk of the steering wire cutting into a softer bending section material due to higher forces.

To sum up, the present disclosure relates to an endoscope comprising: a distal tip unit, a proximal endoscope handle, an endoscope shaft comprising a bending section, a working channel and a steering wire for controlling a bending movement of the bending section. The bending section is made of a first material and comprises a plurality of segments, flexible hinge members provided between adjacent segments, an inner lumen adopted for accommodating the working channel and steering wire lumens adapted for accommodating the steering wire. The endoscope further comprises a disc made of a second material, which is different from the first material. The disc is arranged in the distal end/the distal end segment adjacent a lumen end of the steering wire lumens and has a plurality of openings. The openings comprise steering wire lumen openings configured for guiding the steering wire coming from the steering wire lumens there through, and locking openings configured for threading or twisting the steering wire there through. The steering wire is locked to the disc by the threading or twisting of the steering wire through the openings.

BRIEF DESCRIPTION OF FIGURES

The disclosure is explained in more detail below using preferred embodiments and referring to the accompanying figures.

The figures are schematic in nature and serve only to understand the disclosure. Identical elements are marked with the same reference signs. The features of the different embodiments can be interchanged among each other.

DETAILED DESCRIPTION OF PREFERRED EMBODIMENTS

Figure 1:
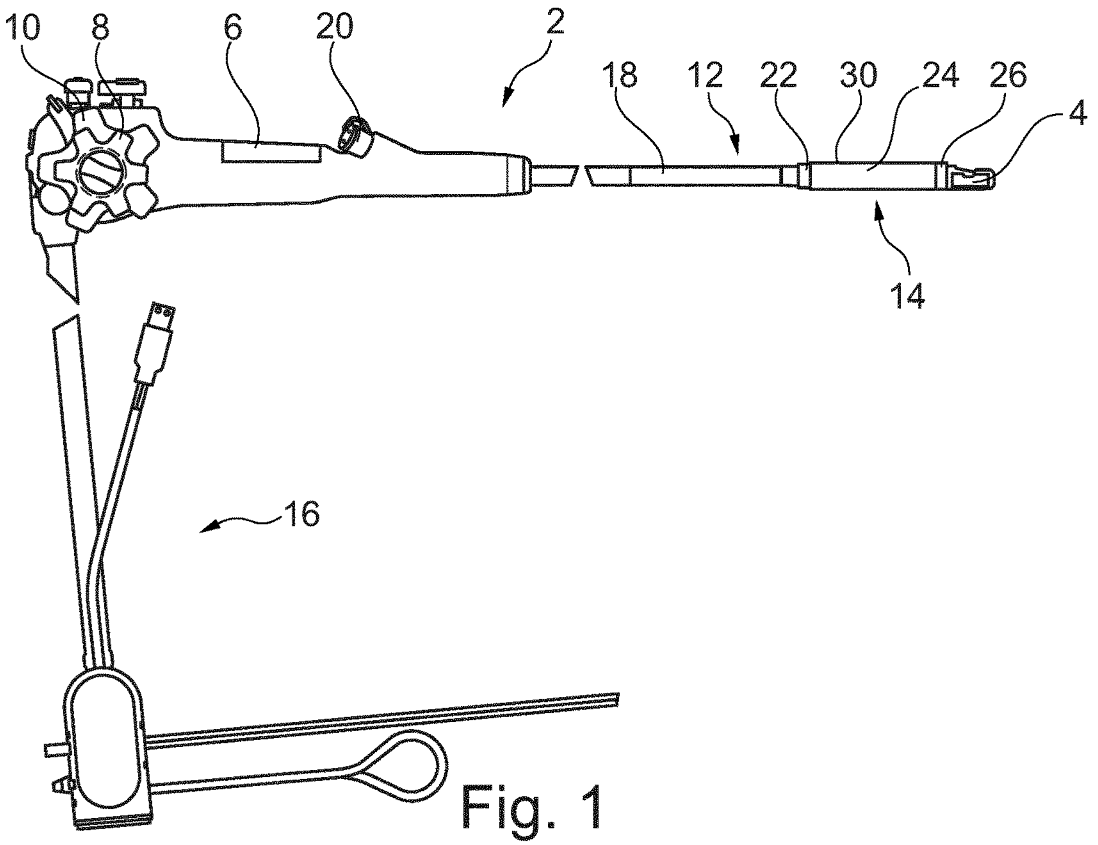
FIG. 1 is a plan view showing an endoscope according to the present disclosure.

In FIG. 1, an endoscope 2 is shown. The endoscope 2 is preferably a single-use endoscope. The endoscope 2 comprises a distal tip unit 4, which is configured to be inserted into a patient's body cavity. Further, the endoscope 2 comprises a proximal endoscope handle (handle unit) 6 designed to be held by a user/physician and being configured as a housing for accommodating operating parts (not shown) of the endoscope 2. The endoscope handle 6 comprises two handle wheels (operating units), namely a first handle wheel 8 and a second handle wheel 10, for steering the distal tip unit 4. In particular, the first handle wheel 8 and the second handle wheel 10 can both be rotated/turned by the user. The first handle wheel 8 and the second handle wheel 10 are arranged coaxially, i.e. can be rotated around a common rotational axis. The endoscope 2 further comprises an endoscope shaft (insertion tube) 12 extending from the endoscope handle 6 to the distal tip unit 4 and thus connecting the endoscope handle 6 and the distal tip unit 4. The endoscope shaft 12 comprises a bending section 14 at an end portion thereof. Moreover, a connector unit 16 for connecting the endoscope 2 to a supply unit is shown in FIG. 1.

The endoscope 2 has an internal working channel 18, which is formed as a bendable/flexible tube (not shown in FIG. 1). The working channel 18 is provided in/inside the endoscope shaft 12 and extends from the endoscope handle 6 towards the distal tip unit 4. The working channel 18 is accessible via an access port 20. In particular, a surgical instrument may be guided through the working channel 18 into the patient's body cavity via the access port 20. The user/physician is thus able to perform medical operations such as examinations within the patient's body cavity with the surgical instrument.

The distal tip unit 4 may be tilted/bent/moved by bending the bending section 14 of the endoscope shaft 12. The endoscope 2 shown in FIG. 1 is basically a two-plane bending endoscope. This means that the distal tip unit 4 may bend in a first bending plane (e.g. in an up-and-down direction) and in a second bending plane (e.g. in a right-and-left direction). In particular, one of the handle wheels 8, 10, e.g. the first handle wheel 8, can be operated by the user to bend the distal tip unit 4 in the first bending plane and the other one of the handle wheels 8, 10, e.g. the second handle wheel 10, can be operated by the user to bend the distal tip unit 4 in the second bending plane. The first bending plane is preferably perpendicular to the second bending plane.

The bending section 14 comprises a plurality of segments including a proximal end segment 22, a plurality of intermediate segments 24 and a distal end segment 26. Two adjacent segments among the plurality of segments, i.e. a pair of segments, are connected via corresponding flexible hinge members 28, respectively. In particular, two hinge members 28 are formed between two segments. As can best be seen in FIG. 2, hinge members 28 between adjacent pairs of segments are shifted by 90°. E.g. hinge members 28 between the distal end segment 26 and an adjacent (first) intermediate segment 24 are formed at twelve and six when considering the round/circular segments as a clock, and hinge members 28 between the (first) intermediate segment 24 and an adjacent (second) intermediate segment 24 are formed at three and nine when considering the round/circular segments as a clock, and so on. Arranging the hinge members 28 like that makes it possible to bend the bending section 14 in the first bending plane and in the second bending plane. The bending section 14 essentially has a cylindrical shape/a round/circular cross-sectional shape. Referring again to FIG. 1, the bending section 14 may be largely covered by a flexible cover 30 for preventing contamination.

The endoscope 2 comprises two steering wires 32 for controlling the bending movement of the bending section 14. One steering wire 32 of the two steering wires 32 is connected to the first handle wheel 8 and the other one of the two steering wires 32 is connected to the second handle wheel 10. The steering wires 32 extend through the endoscope shaft 12. Each of the two steering wires 32 forms a loop and is thus fixed/locked in a distal end portion of the bending section 14, in particular in the distal end segment 26. By turning the first handle wheel 8, the first steering wire 32 can be pulled and released and the distal tip unit 4 tilts according to a direction in which the first handle wheel 8 is rotated. In other words, by operating the handle wheel 8 the user is able to tilt the distal tip unit 4 in the first bending plane by bending the bending section 14 correspondingly. By turning the second handle wheel 10, the second steering wire 32 can be pulled and released and the distal tip unit 4 tilts according to a direction in which the second handle wheel 10 is rotated. In other words, by operating the handle wheel 10 the user is able to tilt the distal tip unit 4 in the second bending plane by bending the bending section 14 correspondingly.

At the distal tip unit 4, image capturing means such as a miniature video camera and illuminating means such as light-emitting diodes or fiber optic light guides connected to a proximal source of light may be arranged/installed, such that the patient's body cavity can be illuminated and inspected.

Figure 2:
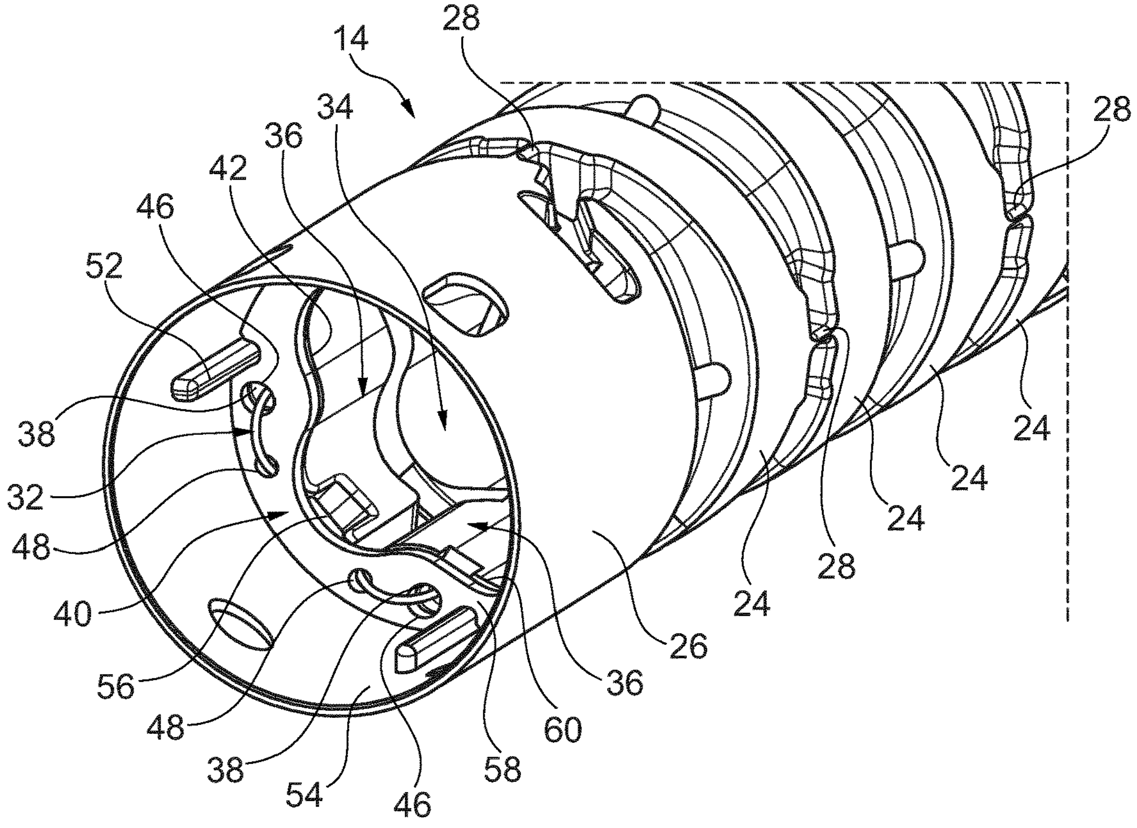
FIG. 2 is a perspective view of a distal end portion of a bending section of the endoscope according to a first preferred embodiment.

FIG. 2 is a perspective view of a distal end portion of a bending section 14 of the endoscope 2 according to a first preferred embodiment. In particular, in FIG. 2 four intermediate segments 24 and the distal end segment 26 of the bending section 14, as well as hinge members 28 between the respective segments can be seen. The bending section 14 further comprises an inner lumen 34, which is a central passage through the segments, i.e. the proximal end segment 22, the intermediate segments 24 and the distal end segment 26. The working channel 18 may be accommodated in the inner lumen 34 of the bending section 14. The inner lumen 34 has a four-leaf clover cross sectional shape. Further, the bending section 14 comprises four dedicated steering wire lumens 36 arranged equally spaced around a circumference of the bending section 14. The steering wire lumens 36 accommodate the steering wires 32 in an assembled state of the endoscope 2. As can be seen in FIG. 2, a lumen end 38 of each steering wire lumen 36 is provided in the distal end segment 26 of the bending section 14. The bending section 14 is a one-piece injection-molded polymer material part, as is typically the case for single-use endoscopes.

As can be further seen in FIG. 2, a separate locking disc 40, preferably made of metal, is inserted into the distal end segment 26 of the bending section 14. The locking disc 40 abuts on a distal surface 42 of the distal end segment 26 and is arranged adjacent the lumen ends 38 of the steering wire lumens 36.

Figure 3:
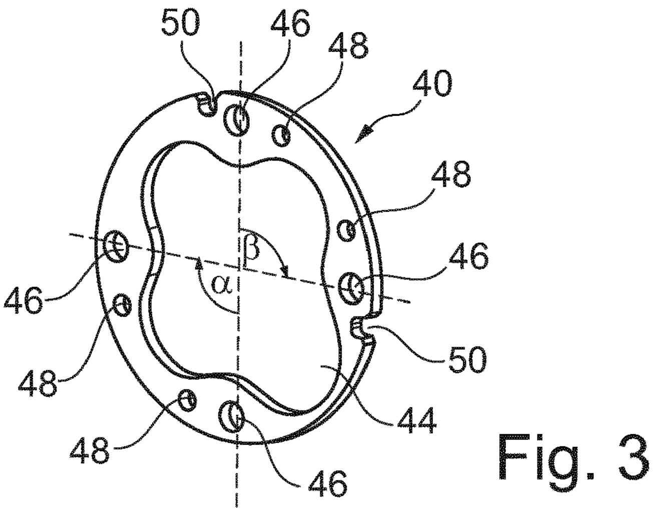
FIG. 3 is a perspective view of a disc inserted in the distal end portion of the bending section according to the first preferred embodiment.

The locking disc 40 according to the first preferred embodiment is shown in FIG. 3 in a perspective view. The locking disc 40 has a round or annular shape with a large center opening 44. The center opening 44 has a four-leaf clover shape corresponding to the shape of the inner lumen 34 of the bending section 14. Moreover, the locking disc 40 has four round/circular steering wire lumen openings 46, which are arranged equally spaced around a circumference of the locking disc 40. In addition, the locking disc 40 has four round/circular locking openings 48. A diameter of the steering wire lumen openings 46 is greater than a diameter of the locking openings 48. In a first angular area α between two steering wire lumen openings 46 two locking openings 48 are provided. Further, in a second angular area β between two other steering wire lumen openings 48 two locking openings 46 are provided. As can be seen in FIG. 3, the first angular area α is arranged diametrically opposed with respect to the second angular area β. The locking disc 40 further comprises two recesses 50 in its outer circumference.

Each recess 50 is provided adjacent a steering wire lumen opening 46. The locking disc 40 has a thickness of about 0.3 mm.

Referring again to FIG. 2, it can be seen that the distal end segment 26 comprises two alignment ribs 52 formed as axially extending protrusions on an inner shell surface 54 thereof. The recesses 50 accommodate the alignment ribs 52, so that the locking disc 40 is accommodated in the distal end segment 26 in a twist-proof way. Said differently, the recesses 50 and the alignment ribs 52 assist in aligning the locking disc 40 with respect to the distal end segment 26 of the bending section 14. The alignment ribs 52 may also serve to align the distal tip unit 4 with respect to the endoscope shaft 12, when the distal tip unit 4 is inserted into the distal end segment 26 of the bending section 14.

As can be further seen in FIG. 2, when the locking disc 40 and the distal end segment 26 are appropriately aligned, the steering wire lumen openings 46 of the locking disc 40 are placed directly over/above/adjacent the lumen ends 38 of the steering wire lumens 36. Said differently, the steering wire lumen openings 46 in a way constitute an extension of the steering wire lumens 36 and the steering wire lumen openings 46 have essentially the same size and shape as the steering wire lumens 46 (seen in a cross sectional view).

In FIG. 2, only one steering wire 32 is visible. A middle section 56 of the steering wire 32 is locked to the locking disc 40, as will be further explained below. A first end section of the steering wire 32 extends from the locking disc 40 through a first steering wire lumen 36 and a second end section of the steering wire 32 extends from the locking disc 40 through a second steering wire lumen 36. As already explained, the two end sections of the steering wire 32 are fixed to one of the two handle wheels, e.g. to the first handle wheel 8. This description applies mutatis mutandis for the second steering wire 32.

The fixation/locking of the steering wire 32 to the locking disc 40 will be further explained. In particular, the steering wire 32 coming from a first steering wire lumen 36 of the bending section 14 and from a first steering wire lumen opening 46 of the locking disc 40 is guided over/along a distal surface 58 of the locking disc 40, is threaded into a first locking opening 48 of the locking disc 40, is guided over/along a proximal surface 60 of the locking disc 40, is threaded into a second locking opening 48 of the locking disc 40, is guided over the distal surface 58 of the locking disc 40 again, and is then threaded into a second steering wire lumen opening 46 of the locking disc 40 and into a second steering wire lumen 36 of the bending section 14. In this way, the steering wire 32 is fixed/locked/fixated to the locking disc 40 by this threading/twisting of the steering wire 32 through the steering wire lumen openings 46 and the locking openings 48 of the locking disc 40. Also this description applies mutatis mutandis for the second steering wire 32.

Figure 4:
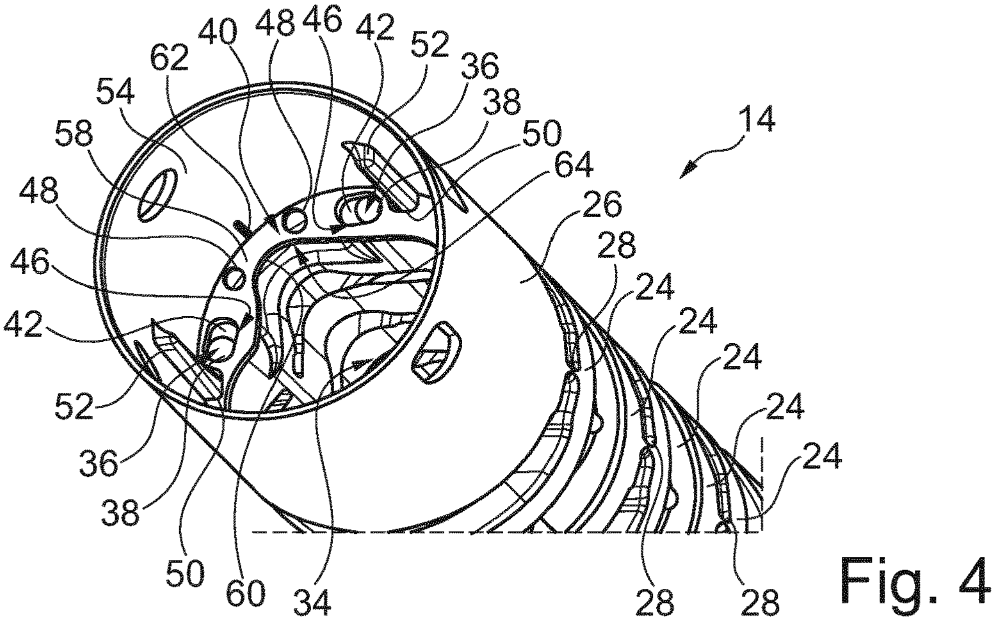
FIG. 4 is a perspective view of a distal end portion of a bending section of the endoscope according to a second preferred embodiment.

FIG. 4 is a perspective view of a distal end portion of a bending section 14 of the endoscope 2 according to a second preferred embodiment. In the following differences with respect to the first preferred embodiment are described. Moreover, features which can be better seen in the perspective view of FIG. 4 will be described. Apart from that, the above description relating to the first preferred embodiment applies mutatis mutandis for the second preferred embodiment and is thus not repeated.

Figure 5:
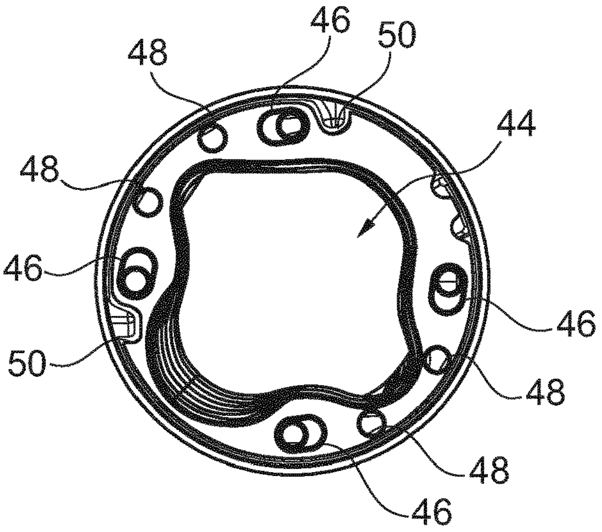
FIG. 5 is a plan view of the distal end portion of the bending section according to the second preferred embodiment.

The main difference of the second preferred embodiment compared to the first preferred embodiment is that the steering wire lumen openings 46 of the locking disc 40 do not have a circular/round shape but an oval/elongated hole/slotted hole shape with semicircles at their respective ends. In particular, the semicircles of the slotted hole shaped steering wire lumen openings 46 have the same radius as the round/circular steering wire lumen end 38. As can be better seen in the plan view of FIG. 5, when the locking disc 40 is inserted into the distal end segment 26 of the bending section 14, one semicircle at an end of the steering wire lumen opening 46 coincides with a semicircle formed by the steering wire lumen end 38 of the steering wire lumen 36, seen in the plan view.

When the locking disc 40 has the elongated hole shaped steering wire lumen openings 46, the steering wire 32 will bend twice/will have two kinks when exiting the steering wire lumen 36. In particular, a first kink is formed when the steering wire 32 is guided via an edge provided between the steering wire lumen 36 and the distal surface 42 of the distal end segment 26 of the bending section 14, and a second kink is formed when the steering wire 32 is then guided via an edge formed by the steering wire lumen opening 46 of the locking disc 40 having the elongated/slotted hole shape towards a locking opening 48. Therefore, according to the second preferred embodiment a radius of the 90° bend where the steering wire 32 enters or leaves the steering wire lumen 36 is larger compared to the first preferred embodiment and the steering wire 32 is supported both by the locking disc 40 and by the distal surface 42 of the distal end segment 26 of the bending section 14.

Moreover, as can be better seen in FIG. 4, the distal end segment 26 of the bending section 14 preferably also comprises four press fit ribs 62 for establishing a press fit connection between an outer circumference of the locking disc 40 and the distal end segment 26. The press fit rib 62 is formed as an axially extending protrusion and is provided on the inner shell surface 54 of the distal end segment 26 of the bending section 14. As can be seen in FIG. 4, an extension of the press fit rib 62 towards the inside of the distal end segment 26 is smaller than an extension of the aligning rib 52 towards the inside of the distal end segment 26. Press fit ribs 62 may also be provided in the first preferred embodiment, in order to axially fix the locking disc 40 within the distal end segment 26.

As can be also better seen in FIG. 4, the distal end segment 26 further comprises a wire cutout 64. The wire cutout 64 is a recessed portion with respect to the distal surface 42 of the distal end segment 26 and is provided under/adjacent the locking openings 48 of the locking disc 40 (in an axial direction of the distal end segment 26).

LIST OF REFERENCE SIGNS

2 endoscope
4 distal tip unit
6 endoscope handle
8 first handle wheel
10 second handle wheel
12 endoscope shaft
14 bending section
16 connector unit
18 working channel
20 access port
22 proximal end segment
24 intermediate segment
26 distal end segment
28 hinge members
30 flexible cover
32 steering wire
34 inner lumen

36 steering wire lumen
38 lumen end
40 locking disc
42 distal surface (of distal end segment)
44 center opening
46 steering wire lumen opening
48 locking opening
50 recess
52 alignment rib
54 inner shell surface
56 middle section
58 distal surface (of locking disc)
60 proximal surface (of locking disc)
62 press fit rib
64 wire cutout

The invention claimed is:

1. An endoscope comprising:

a handle;

a shaft connected to the handle and comprising a bending section, the bending section made of a first material and comprising segments including a proximal end segment, a distal end segment and intermediate segments between the proximal end segment and the distal end segment, the segments interconnected by hinge members configured to articulate the segments, the bending section further comprising an inner lumen configured to accommodate a working channel tube;

a distal tip connected to the distal end segment of the bending section of the shaft;

a first steering wire comprising a first end section, a second end section, and a middle section between the first end section and the second end section, the first end section and the second end section extending from the handle to the middle section of the first steering wire, and the middle section of the first steering wire being positioned in the distal end segment of the bending section; and a disc made of a second material different from the first material, the disc comprising a proximal surface, a distal surface, and four through-holes extending from the proximal surface to the distal surface, wherein the disc is positioned in the distal end segment of the bending section and proximally of the distal tip, the distal end segment being one of the segments interconnected by the hinge members to articulate the segments, and wherein the first steering wire is locked to the disc by passing through the four through-holes of the disc, a portion of the middle section of the first steering wire extending between two of the four through-holes proximally of the proximal surface of the disc.

2. The endoscope of claim 1, wherein the four through-holes of the disc comprise a first pair of locking openings and a first pair of steering wire lumen openings, the first pair of locking openings being positioned between steering wire lumen openings of the first pair of steering wire lumen openings.

3. The endoscope of claim 2, wherein the first pair of locking openings comprises a first locking opening and a second locking opening, wherein the first pair of steering wire lumen openings comprises a first steering wire lumen opening and a second steering wire lumen opening, and wherein the first steering wire is threaded through the first steering wire lumen opening over the distal surface and into the first locking opening, over the proximal surface into the second locking opening, and over the distal surface and into the second steering wire lumen opening.

4. The endoscope of claim 3, wherein the middle section is threaded through the disc, wherein the first end section extends from the disc through a first steering wire lumen of the steering wire lumens, and wherein the second end section extends from the disc through a second steering wire lumen of the steering wire lumens.

5. The endoscope of claim 3, further comprising a second steering wire, the disc further comprising a second pair of steering wire lumen openings and a second pair of locking openings, wherein:

the second pair of locking openings comprise a third locking opening and a fourth locking opening, the second pair of steering wire lumen openings comprise a third steering wire lumen opening and a fourth steering wire lumen opening, the second pair of locking openings positioned between the third steering wire lumen opening and the fourth steering wire lumen opening, and the second steering wire is threaded through the third steering wire lumen opening over the distal surface and into the third locking opening, over the proximal surface into the fourth locking opening, and over the distal surface and into the fourth steering wire lumen opening.

6. The endoscope of claim 5, wherein the first pair of steering wire lumen openings and the first pair of locking openings are positioned in a first angular area (α), and wherein the second pair of steering wire lumen openings and the second pair of locking openings are positioned in a second angular area (β), the first angular area (α) being diametrically opposed with respect to the second angular area (β).

7. The endoscope of claim 1, wherein the distal end segment of the bending section of the shaft comprises an inner shell surface and an alignment rib extending inwardly from the inner shell surface, wherein the disc comprises a recess, and wherein the recess receives the alignment rib to align the disc in the distal end of the bending section.

8. The endoscope of claim 1, wherein the distal end segment comprises an inner shell surface, an alignment rib extending inwardly from the inner shell surface, and a press fit rib extending inwardly from the inner shell surface, wherein the disc comprises a recess, wherein the recess receives the alignment rib to align the disc in the distal end of the bending section, and wherein the press fit rib establishes a press fit connection between an outer circumference of the disc and the distal end segment.

9. The endoscope of claim 1, wherein the second material is harder or more rigid than the first material.

10. The endoscope of claim 9, wherein the first material is a polymer material and the second material is a metal material.

11. The endoscope of claim 1, wherein the disc abuts a distal surface provided in the distal end segment of the bending section.

12. The endoscope of claim 1, wherein the four through-holes of the disc comprise a first pair of locking openings and a first pair of steering wire lumen openings, wherein the distal end segment of the bending section comprises a wire cutout, the wire cutout being a recessed portion with respect to the distal surface of the disc and being provided in a circumferential area of the distal end segment where the first pair of locking openings are provided.

13. The endoscope of claim 1, wherein the four through-holes of the disc include a first pair of steering wire lumen openings, and wherein each steering wire lumen opening of the first pair of steering wire lumen openings has an elongated hole shape.

14. The endoscope of claim 1, wherein the four through-holes of the disc include a first pair of steering wire lumen openings, wherein the first steering wire has a first kink and a second kink, wherein the first kink is formed by the first steering wire running via an edge provided between a steering wire lumen opening of the first pair of steering wire lumen openings and the distal surface, and wherein the second kink is formed by the first steering wire running via an edge formed by the other of the steering wire lumen openings of the first pair of steering wire lumen openings.

15. The endoscope of claim 1, wherein the distal end segment of the bending section comprises an alignment rib, and wherein the disc comprises a recess receiving the alignment rib.

16. The endoscope of claim 15, wherein the distal end segment of the bending section comprises a press fit rib configured to establish a press fit connection with an outer circumference of the disc.

17. The endoscope of claim 1, wherein the bending section comprises steering wire lumens, and wherein a portion of the middle section of the first steering wire is positioned longitudinally between the disc and the steering wire lumens.

18. The endoscope of claim 1, further comprising a first wheel and a second wheel, the first wheel being connected to the first end section of the first steering wire and configured to translate the first end section of the first steering wire to bend the bending section along a first bending plane, and the second wheel being connected to the second end section of the first steering wire and configured to translate the second end section of the first steering wire to bend the bending section along a second bending plane, wherein the second bending plane is different from the first bending plane.

* * * * *